US00PP18528P2

(12) United States Plant Patent
Bennett

(10) Patent No.: US PP18,528 P2
(45) Date of Patent: Feb. 26, 2008

(54) REDBUD TREE NAMED 'CASCADING HEARTS'

(50) Latin Name: *Cercis canadensis*
Varietal Denomination: Cascading Hearts

(75) Inventor: Steven E. Bennett, Thompsons Station, TN (US)

(73) Assignee: Riverbend Nurseries, Thompsons Station, TN (US)

( * ) Notice: Subject to any disclaimer, the term of this patent is extended or adjusted under 35 U.S.C. 154(b) by 0 days.

(21) Appl. No.: 11/269,180

(22) Filed: Nov. 8, 2005

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
(74) *Attorney, Agent, or Firm*—C. A. Whealy

(57) ABSTRACT

A new and distinct cultivar of Redbud tree named 'Cascading Hearts', characterized by its weeping plant form; densely foliated growth habit; and developing leaves reddish green in color; fully expanded leaves, dark green in color.

2 Drawing Sheets

Botanical designation: *Cercis canadensis.*
Cultivar denomination: 'Cascading Hearts'.

BACKGROUND OF THE INVENTION

The present Invention relates to a new and distinct cultivar of Redbud tree, botanically known as *Cercis canadensis,* and hereinafter referred to by the name 'Cascading Hearts'.

The new Redbud tree is a naturally-occurring whole plant mutation of an unnamed selection of *Cercis canadensis,* not patented. The new Redbud tree was discovered and selected by the Inventor in October, 1997 as a single plant within a population of trees of the parent selection in a controlled environment in Thompsons Station, Tenn.

Asexual reproduction of the new Redbud tree by terminal cuttings in a controlled environment in Thompsons Station, Tenn. since August, 2003, has shown that the unique features of this new Redbud tree are stable and reproduced true to type in successive generations.

SUMMARY OF THE INVENTION

The new Redbud tree has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Cascading Hearts'. These characteristics in combination distinguish 'Cascading Hearts' as a new and distinct cultivar:

1. Weeping plant form.
2. Densely foliated growth habit.
3. Developing leaves reddish green in color; fully expanded leaves, dark green in color.

In side-by-side comparisons conducted in Thompsons Station, Tenn., trees of the new Redbud tree differed from trees of the unnamed parent selection of *Cercis canadensis* primarily in plant habit as trees of the parent selection were upright and not weeping.

Trees of the new Redbud can be compared to trees of the Redbud cultivar Traveller, disclosed in U.S. Plant Pat. No. 8,640. In side-by-side comparisons conducted in Thompsons Station, Tenn., trees of the new Redbud differed primarily from trees of the cultivar Traveller in hardiness as trees of the new Redbud were hardier than trees of the cultivar Traveller.

Trees of the new Redbud can also be compared to trees of the Redbud cultivar Covey, disclosed in U.S. Plant Pat. No. 10,328. In side-by-side comparisons conducted in Thompsons Station, Tenn., trees of the new Redbud differed primarily from trees of the cultivar Covey in plant form as trees of the new Redbud were more densely foliated than trees of the cultivar Covey. In addition, trees of the new Redbud were less susceptible to sunscald than trees of the cultivar Covey.

BRIEF DESCRIPTION OF THE PHOTOGRAPHS

The accompanying colored photographs illustrate the overall appearance of the new Redbud tree. These photographs show the colors as true as it is reasonably possible to obtain in colored reproductions of this type. Colors in the photographs may differ slightly from the color values cited in the detailed botanical description, which accurately describe the colors of the new Redbud tree.

The photograph on the first sheet comprises a side perspective view of a typical tree of 'Cascading Hearts'.

The photograph on the second sheet is a close-up view of a typical flower of 'Cascading Hearts'.

DETAILED BOTANICAL DESCRIPTION

The aforementioned photographs and following observations and measurements describe trees grown in Thompsons Station, Tenn., in an outdoor nursery and under commercial production conditions. During the production of the trees, day temperatures ranged from 8° C. to 33° C. and night temperatures ranged from −3° C. to 19° C. Trees used for the photographs were about five years old and trees used for the description were about two years old.

In the following description, color references are made to The Royal Horticultural Society Colour Chart, 1995 Edition, except where general terms of ordinary dictionary significance are used.

Botanical classification: *Cercis canadensis* 'Cascading Hearts'.

Parentage: Naturally-occurring whole plant mutation of an unnamed selection of *Cercis canadensis,* not patented.

Propagation:

*Type.*—By cuttings.

*Time to produce a rooted young plant.*—About four to six weeks.

*Root description.*—Fine, fibrous; white in color.

*Rooting habit.*—Freely branching.

Plant description:

*Plant form and growth habit.*—Perennial, deciduous tree; weeping plant habit; densely foliated; moderately vigorous to vigorous growth habit.

*Branching habit.*—Freely branching, lateral branches potentially developing at every node.

*Plant height.*—About 90 cm.

*Plant diameter, area of spread.*—About 110 cm.

*Trunk.*—Diameter, at base: About 15 cm. Texture: Smooth, glabrous. Color: Close to 197B.

*Lateral branch description.*—Length: About 52 cm. Diameter: About 7 mm. Internode length: About 4 cm. Strength: Very strong. Texture, developing: Smooth, glabrous. Texture, mature: Woody; slightly rough, glabrous. Color, developing: Close to 187A. Color, mature: Close to 200A. Lenticels: Length: About 1.5 mm. Diameter: Less than 1 mm. Shape: Oval. Color: Close to 196D.

*Foliage description.*—Arrangement: Alternate, single. Length: About 7.2 cm. Width: About 8.4 cm. Shape: Mostly cordate. Apex: Mostly acute. Base: Cordate. Margin: Entire. Venation pattern: Palmate. Texture, upper and lower surfaces: Leathery, durable; smooth, glabrous. Color: Developing foliage, upper surface: 147A overlain with close to 187A. Developing foliage, lower surface: Close to 147B. Fully expanded foliage, upper surface: Close to 147A. Fully expanded foliage, lower surface: Close to 147B. Venation, upper surface: Close to 147A. Venation, lower surface: Close to 147B to 147C. Petiole: Length: About 3.7 cm. Diameter: About 2 mm. Texture, upper and lower surfaces: Smooth, glabrous. Color, upper and lower surfaces: Close to 144A.

Flower description:

*Natural flowering season.*—Early spring in Tennessee. Flowers not persistent.

*Flower arrangement.*—Flowers axillary and in clusters of two to three. Flowers face mostly outward.

*Fragrance.*—None detected.

*Flower diameter.*—About 2.5 cm.

*Flower depth.*—About 3 cm.

*Longevity.*—Flowers last about one week on the plant depending on rainfall, wind and temperature.

*Flower buds.*—Length: About 3 mm. Diameter: About 1.5 mm. Color: Close to 76C.

*Petals.*—Arrangement: Papillonaceous with five petals, three upper banner petals and lower two petals fused into a keel. Length, banner and keel: About 1.2 cm. Width, banner and keel: About 7.5 mm. Shape: Ligulate with rounded apex. Margin: Mostly entire. Texture, upper and lower surfaces: Smooth, glabrous; satiny. Color, banner and keel: When opening and fully opened, upper surface: Close to 76A; venation, close to 77A. When opening and fully opened, lower surface: Close to 76A to 76B.

*Calyx.*—Shape: Campanulate, fused at base. Length: About 1 mm. Diameter: About 3 mm. Color: Close to 71B to 71C.

*Peduncles.*—Length: About 5 mm. Diameter: About 1 mm. Strength: Flexible; strong. Texture: Smooth, pubescent. Color: Close to 144A to 144B.

*Reproductive organs.*—Androecium: Quantity of stamens per flower: Ten. Anther length: Less than 1 mm. Anther shape: Oblong. Anther color: Close to 6A. Amount of pollen: None observed. Gynoecium: Quantity of pistils per flower: One. Pistil length: About 2 cm. Style length: About 1.5 cm. Style color: Close to 155D. Stigma diameter: Less than 1 mm. Stigma color: Close to 154D. Ovary color: Close to 144A.

*Seed/fruit.*—Seed and fruit development have not been observed.

Weather/temperature tolerance: Trees of the new Redbud have been observed to be very tolerant to rain and wind. Trees of the new Redbud tree have been observed to be hardy to cold temperature USDA Zone 4A and high temperature USDA Zone 9B.

Disease/pest resistance: Trees of the new Redbud have not been observed to be resistant to pest and other pathogens common to Redbud trees.

It is claimed:

1. A new and distinct Redbud tree named 'Cascading Hearts', as illustrated and described.

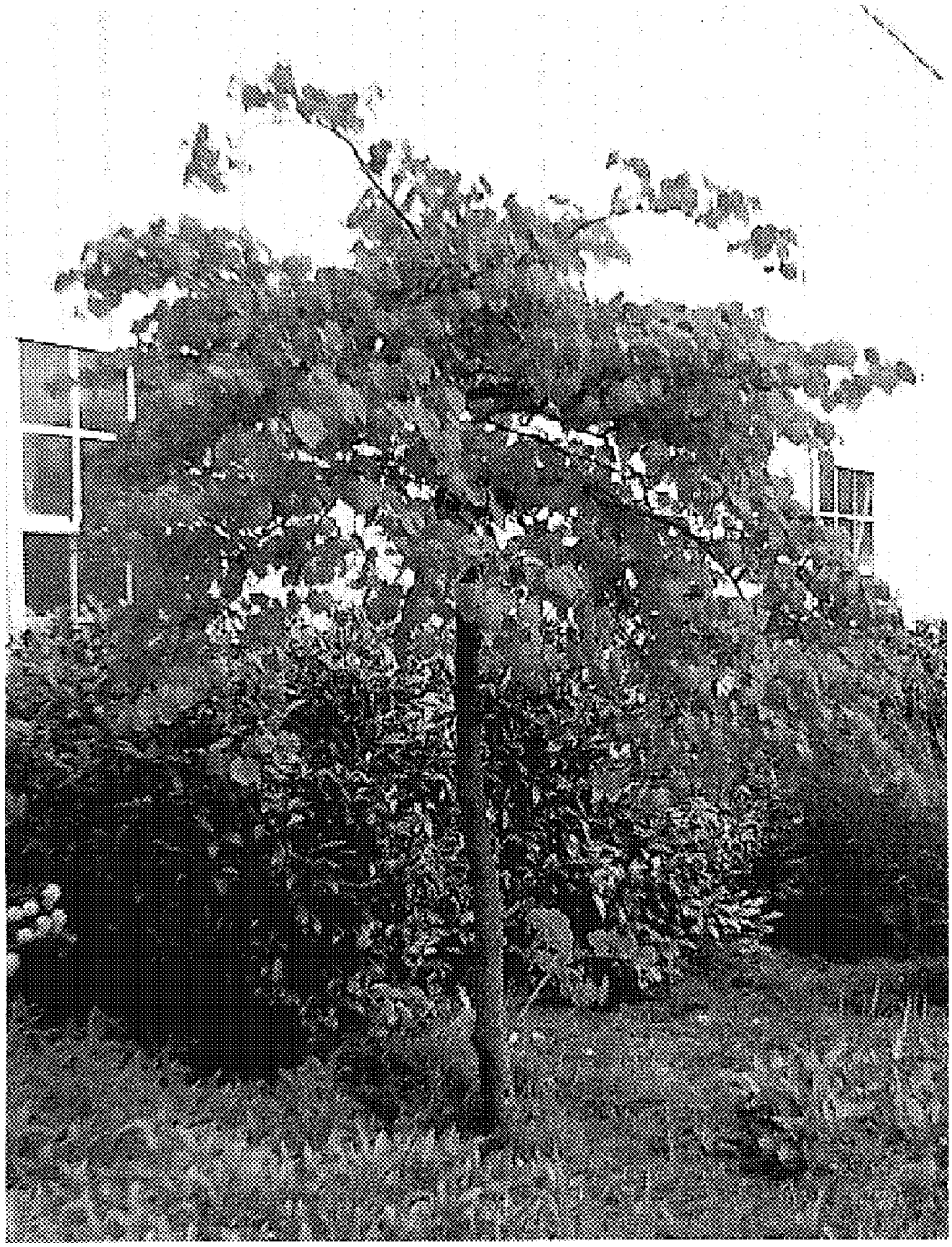

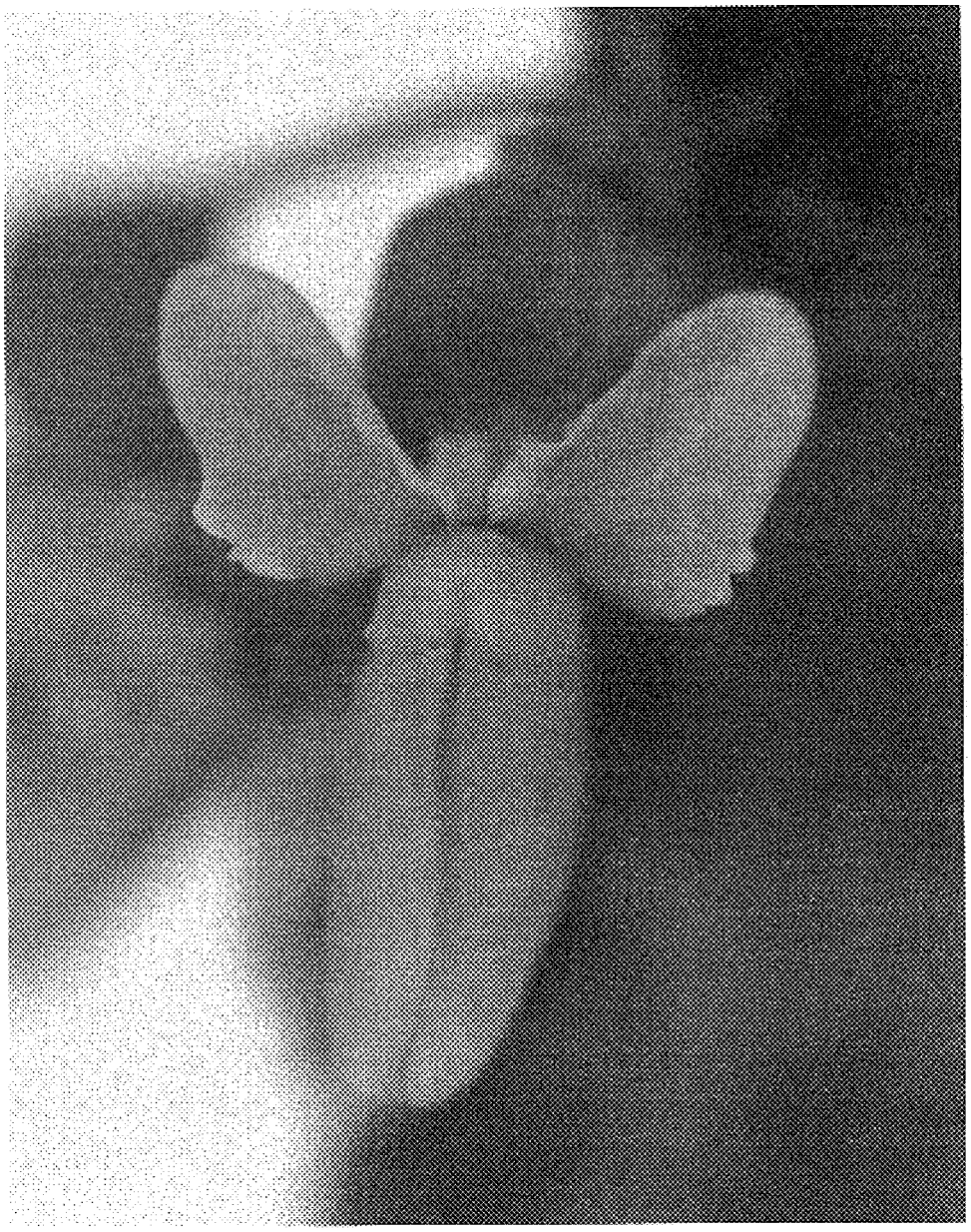

* * * * *